(12) United States Patent
Piran et al.

(10) Patent No.: US 8,178,537 B2
(45) Date of Patent: May 15, 2012

(54) SOLID STATE FORMS OF VARENICLINE SALTS AND PROCESSES FOR PREPARATION THEREOF

(75) Inventors: Maytal Piran, Rishon LeZion (IL); Vinod Kumar Kansal, Faridabad (IN); Suhail Ahmad, New Delhi (IN); Vineet Kumar Tyagi, Ghaziabad (IN); Ayyagari Subramanya Sharma, Greater Noida (IN)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 12/820,553

(22) Filed: Jun. 22, 2010

(65) Prior Publication Data

US 2010/0324055 A1 Dec. 23, 2010

Related U.S. Application Data

(60) Provisional application No. 61/219,099, filed on Jun. 22, 2009, provisional application No. 61/345,300, filed on May 17, 2010.

(51) Int. Cl.
*A61K 31/495* (2006.01)
(52) U.S. Cl. ........................... 514/250; 544/345
(58) Field of Classification Search .................. 514/250; 544/345
See application file for complete search history.

(56) References Cited

U.S. PATENT DOCUMENTS

| | | | |
|---|---|---|---|
| 6,410,550 B1 | 6/2002 | Coe et al. |
| 6,558,435 B2 | 5/2003 | Am Ende et al. |
| 6,605,610 B1 | 8/2003 | Coe et al. |
| 6,787,549 B2 | 9/2004 | Johnson et al. |
| 6,794,388 B2 | 9/2004 | Quallich et al. |
| 6,887,884 B2 | 5/2005 | Coe et al. |
| 6,890,927 B2 | 5/2005 | Bogle et al. |
| 6,897,310 B2 | 5/2005 | Coe et al. |
| 6,951,938 B2 | 10/2005 | Coe et al. |
| 7,009,073 B2 | 3/2006 | Watson et al. |
| 7,091,372 B2 | 8/2006 | Singer et al. |
| 7,144,882 B2 | 12/2006 | Coe et al. |
| 7,186,870 B2 | 3/2007 | Singer et al. |
| 7,205,300 B2 | 4/2007 | Coe et al. |
| 7,265,119 B2 | 9/2007 | Bogle et al. |
| 2002/0072524 A1 | 6/2002 | Wadsworth et al. |
| 2003/0060624 A1 | 3/2003 | Singer |
| 2003/0134844 A1 | 7/2003 | Saltarelli |
| 2003/0166701 A1 | 9/2003 | Bogle et al. |
| 2003/0180360 A1 | 9/2003 | Am Ende et al. |
| 2004/0082555 A1 | 4/2004 | Villalobos |
| 2004/0235850 A1 | 11/2004 | Waterman |
| 2005/0004379 A1 | 1/2005 | Handfield et al. |
| 2005/0250806 A1 | 11/2005 | Saltarelli |
| 2006/0057207 A1 | 3/2006 | Ziegler et al. |
| 2006/0084656 A1 | 4/2006 | Ziegler et al. |
| 2007/0066827 A1 | 3/2007 | Handfield, Jr. et al. |
| 2007/0185327 A1 | 8/2007 | Rainville et al. |
| 2007/0224690 A1 | 9/2007 | Busch et al. |
| 2007/0248671 A1 | 10/2007 | Johnson et al. |
| 2007/0275973 A1 | 11/2007 | Coe et al. |
| 2008/0026059 A1 | 1/2008 | Waterman |

FOREIGN PATENT DOCUMENTS

| | | |
|---|---|---|
| EP | 1157726 | 11/2001 |
| EP | 1 659 114 | 5/2006 |
| WO | WO 99/35131 | 7/1999 |
| WO | WO 01/62736 | 8/2001 |
| WO | WO 01/85688 | 11/2001 |
| WO | WO 02/085843 | 10/2002 |
| WO | WO 02/092089 | 11/2002 |
| WO | WO 02/092597 | 11/2002 |
| WO | WO 03/045394 | 6/2003 |
| WO | WO 03/045437 | 6/2003 |
| WO | WO 2004/046077 | 6/2004 |
| WO | WO 2004/048318 | 6/2004 |
| WO | WO 2004/063164 | 7/2004 |
| WO | WO 2004/108725 | 12/2004 |
| WO | WO 2006/090236 | 8/2006 |
| WO | WO 2006/100595 | 9/2006 |
| WO | WO 2006/117672 | 11/2006 |
| WO | WO 2007/012963 | 2/2007 |
| WO | WO 2007/110730 | 10/2007 |
| WO | WO 2008/060487 | 5/2008 |
| WO | WO 2009/065872 | 5/2009 |
| WO | WO 2009/109651 | 9/2009 |
| WO | WO 2009/143347 | 11/2009 |
| WO | WO 2010/023561 | 3/2010 |

OTHER PUBLICATIONS

Perry's Chemical Engineer's Handbook, 6th ed., pp. 20-54 to 20-57, 1984.
Remington: The Science and Practice of Pharmacy, 19th ed., vol. 2, pp. 1627-1628. (1995).
Anonymous, "1,2,3,4-Tetrahydro-1,4-methano-nepthalene-2,3-diol", Jun. 12, 2008.
"Loss on Drying", "Physical Test and Determination", LPS 29-NF24, Aug. 1, 2006, Physical Test and Determination, The United States Pharmacopeial Convention.
International Search Report and Written Opinion, dated Oct. 1, 2010, from corresponding International Patent Application PCT/US2010/039446.

*Primary Examiner* — James O Wilson
*Assistant Examiner* — Douglas M Willis
(74) *Attorney, Agent, or Firm* — Kenyon & Kenyon LLP

(57) ABSTRACT

Salts and crystalline forms of several salts of Varenicline, i.e., Varenicline sulfate:

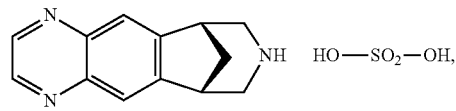

are provided, along with methods of preparing the solid states and processes for preparing Varenicline base from those Varenicline salts.

6 Claims, 6 Drawing Sheets

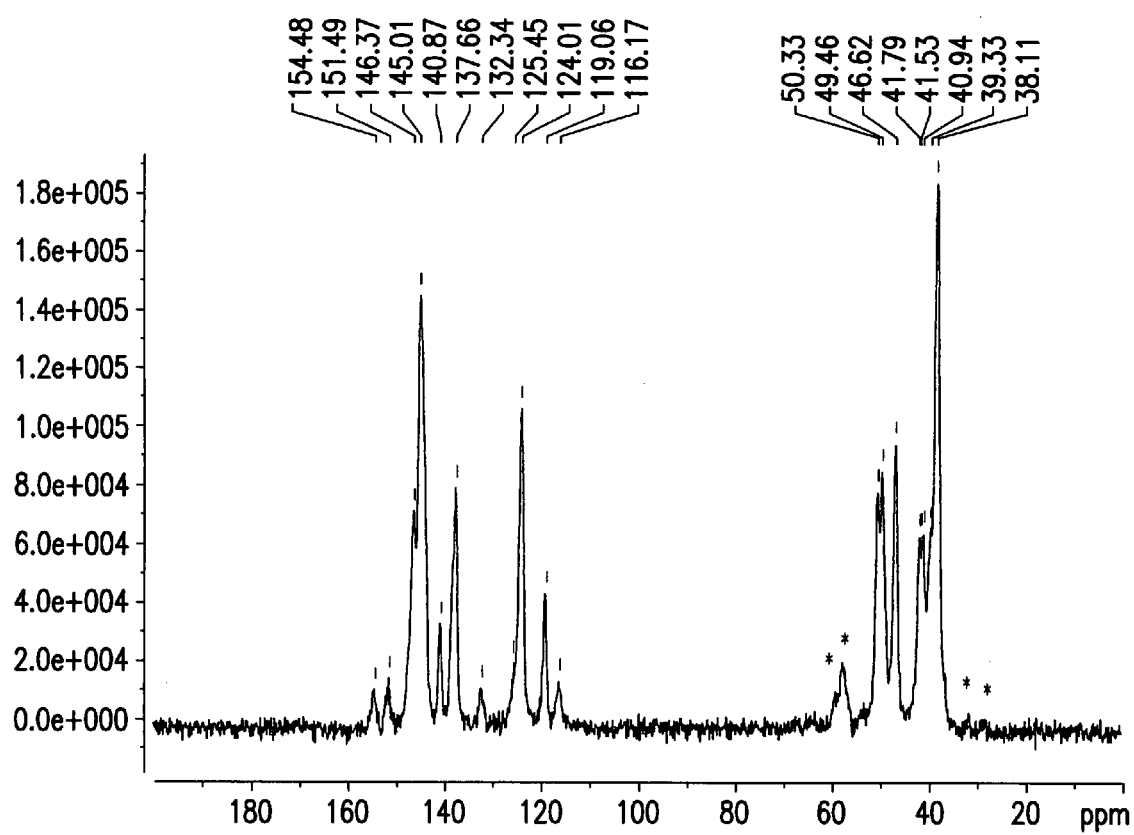
FIG. 1.2

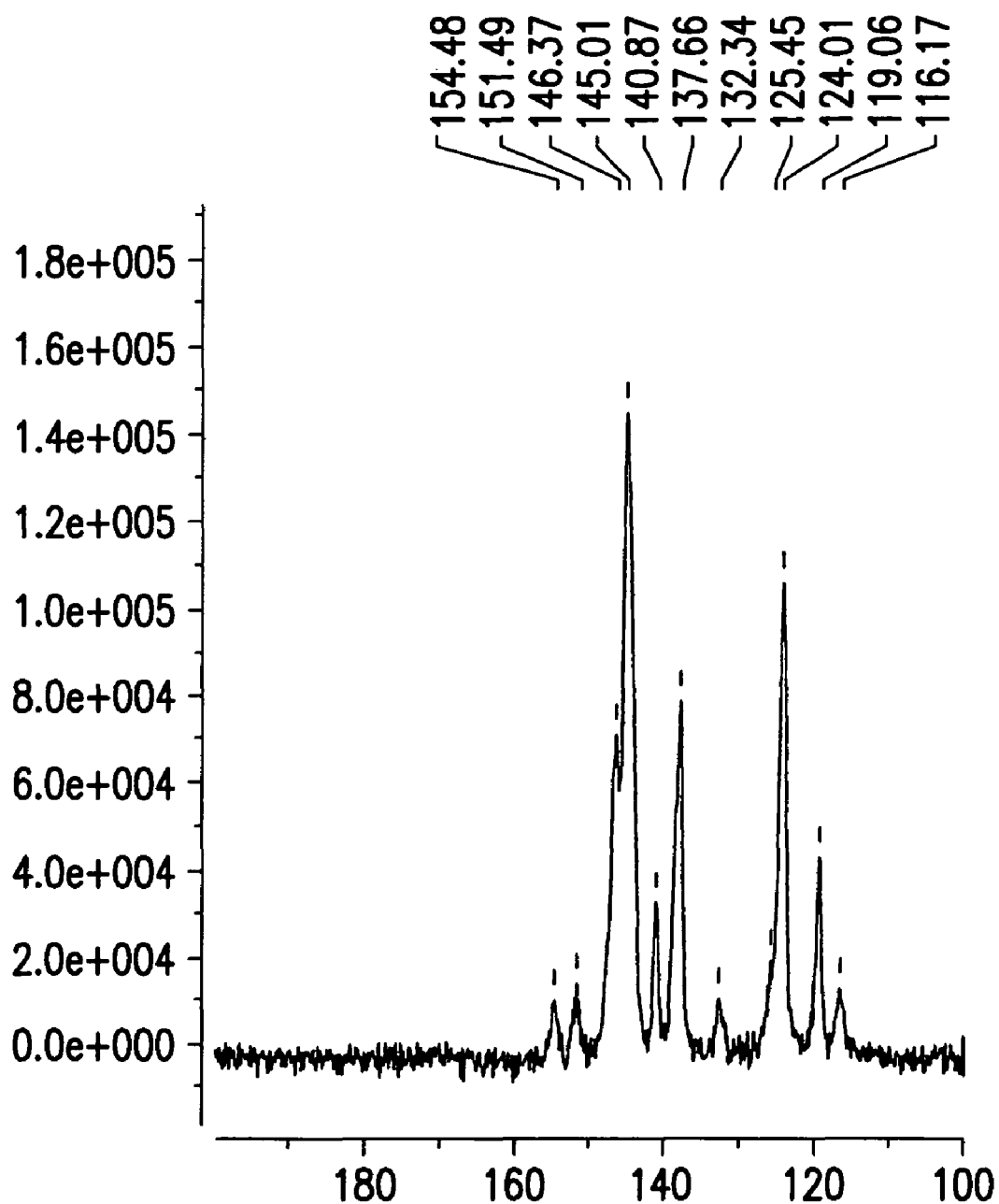
FIG.1.3

SOLID STATE FORMS OF VARENICLINE SALTS AND PROCESSES FOR PREPARATION THEREOF

RELATED APPLICATIONS

This application claims the benefit under 35 U.S.C. §119 (e) of U.S. Provisional Application Nos. 61/219,099, filed Jun. 22, 2009; and 61/345,300, filed May 17, 2010, each of which is incorporated herein by reference in its entirety.

FIELD OF INVENTION

The invention is directed to solid states of Varenicline salts, and methods for the preparation of the solid states.

BACKGROUND OF THE INVENTION

Varenicline tartrate salt, 7,8,9,10-tetrahydro-6,10-methano-6H-pyrazino[2,3-h][3]benzazepine, (2R,3R)-2,3-dihydroxybutanedioate (1:1), has a molecular weight of 361.35 Daltons, and has the following structural formula:

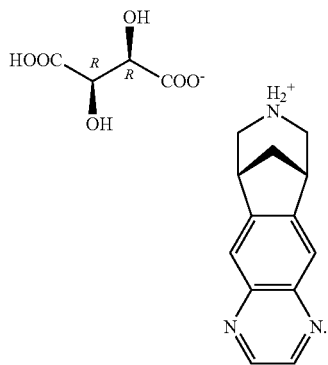

Varenicline tartrate is marketed by Pfizer under the trade name of CHANTIX™ as a partial agonist selective for certain subtypes of nicotinic receptors and indicated for smoking cessation.

Varenicline base, 5,8,14-Triazatetracyclo [$10.3.1.0^{2,11}.0^{4,9}$]hexadeca-2(11),3,5,7,9-pentaene and a variety of salts thereof are disclosed in U.S. Pat. No. 6,410,550, EP 1044189, and EP 1659114.

Varenicline citrate and succinate salts are described in U.S. Pat. Nos. 6,787,549 and 6,794,388, respectively. A Crystalline form of Varenicline fumarate is described in PCT Publication No. WO2009/109651.

Varenicline L-tartrate and its crystalline forms A, B, and C are described in the U.S. Pat. Nos. 6,890,927 and 7,265,119.

SUMMARY OF THE INVENTION

The invention provides salts and crystalline forms of Varenicline salts, and processes for preparing them.

The invention further provides a pharmaceutical formulation comprising the below described salts and crystalline forms of Varenicline salts. This pharmaceutical composition may additionally comprise at least one pharmaceutically acceptable excipient.

The invention further provides the use of the salts and the solid state forms described below for the manufacture of a medicament for the treatment of smoking addiction.

BRIEF DESCRIPTION OF THE FIGURES

FIG. 1.2 shows a solid state $^{13}$C NMR spectrum of Form I of Varenicline Sulfate in the 0-200 ppm range.

FIG. 1.3 shows a solid state $^{13}$C NMR spectrum of Form I of Varenicline Sulfate in the 100-200 ppm range.

DETAILED DESCRIPTION OF THE INVENTION

Figure 1:
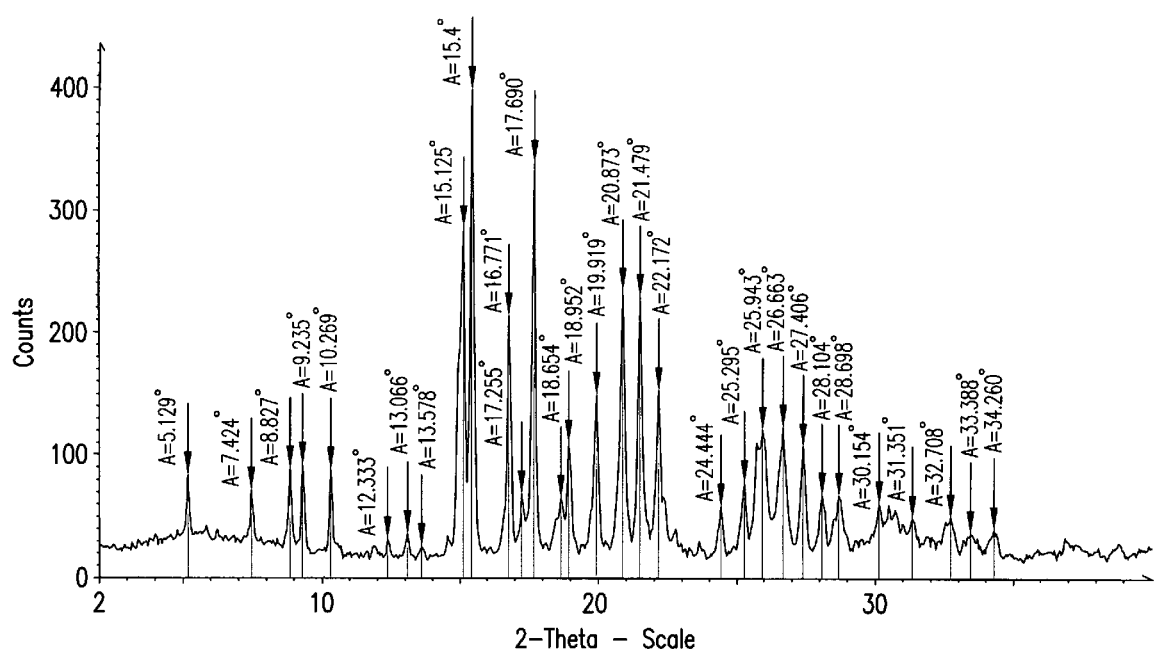
FIG. 1.1 shows a PXRD pattern of crystalline Varenicline Sulfate Form I.

The invention provides novel salts and novel crystalline forms of several salts of Varenicline, i.e., Varenicline sulfate, Varenicline mesylate, and Varenicline fumarate. The invention also provides methods of preparing the solid states of Varenicline sulfate, Varenicline mesylate, and Varenicline fumarate, and processes for preparing Varenicline base from those Varenicline salts.

In some embodiments, the polymorphs of Varenicline salts of the invention are substantially free of any other polymorphic forms. By "substantially free" is meant that the forms of the invention contain 20% (w/w) or less, 10% (w/w) or less, 5% (w/w) or less, 2% (w/w) or less, particularly 1% (w/w) or less, more particularly 0.5% (w/w) or less, and most particularly 0.2% (w/w) or less of any other polymorph. For examples, the polymorphs of the Varenicline salts of the invention contain from 0.1% to 5% (w/w), from 0.2% to 5% (w/w), or from 0.2% to 2% (w/w) of the any other polymorph. In other embodiments, the polymorphs of Varenicline salts of the invention contain from 0.1% to 20% (w/w), from 1% to 20% (w/w), from 5% to 20% (w/w), or from 5% to 10% (w/w) of any other polymorph.

A crystal form may be referred to herein as being characterized by graphical data "as shown in" a Figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

Varenicline sulfate, Varenicline mesylate, and Varenicline fumarate can be isolated as solids and, for examples, as crystal forms. The above salts can be useful as intermediate compounds for preparing Varenicline base, 5,8,14-triazatetracyclo [$10.3.1.0^{2,11}.0^{4,9}$] hexadeca-2(11),3,5,7,9-pentaene, having the following formula:

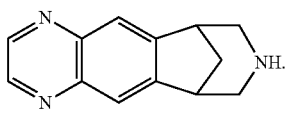

The Varenicline base obtained according to the invention may be further converted to Varenicline L-tartrate salt.

A thing, e.g., a reaction mixture may be characterized as being at, or allowed to come to "room temperature". This expression means that the temperature is close to, or the same as, that of the space, e.g., the room or the fume hood, in which the thing is located. Typically, room temperature is from about 20° C. to about 30° C., or about 25° C.

In one embodiment, the invention provides Varenicline sulfate. The Varenicline sulfate can be isolated. The Varenicline sulfate can be also in a crystalline form.

In another embodiment, the invention provides a crystalline form of Varenicline sulfate, designated Form I. Preferably, Form I is a hemi-sulfate.

The Varenicline sulfate Form I can be characterized by analytical methods such as powder XRD and solid-state $^{13}C$ NMR. Form I is thus characterized by data selected from: a powder XRD pattern having peaks at 15.1°, 15.4°, 16.8°, 17.7°, and 21.5°±0.2 degrees two theta; a powder XRD pattern substantially as shown in FIG. 1.1; a solid-state $^{13}C$ NMR spectrum with signals at 124.0, 137.7, and 145.0±0.2 ppm; a solid-state $^{13}C$ NMR spectrum having chemical shifts differences between the signal exhibiting the lowest chemical shift and another in the chemical shift range of 120 to 180 ppm of 0.0, 13.7, and 21.0±0.1 ppm, wherein the signal exhibiting the lowest chemical shift in the chemical shift area of 120 to 180 ppm is at 124.0±1 ppm; a $^{13}C$ NMR spectrum substantially as shown in FIG. 1.2; and combinations thereof.

The above crystalline form of Varenicline sulfate may be further characterized by additional powder XRD peaks at 10.3°, 19.0°, 19.9°, 21.5°, and 22.2°±0.2 degrees two theta.

Varenicline sulfate salt, and in particular Form I, preferably has advantageous properties selected from at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density. In particular, Form I exhibits high solubility in water.

The crystalline form of Varenicline sulfate may be prepared by a process comprising combining Varenicline base, a $C_1$-$C_6$ alcohol, a $C_6$-$C_{12}$ aromatic hydrocarbon, and sulfuric acid to obtain a reaction mixture, and cooling the obtained reaction mixture to obtain a precipitate.

Examples for the $C_6$-$C_{12}$ aromatic hydrocarbon can be toluene or xylene, where the xylene can be used in the form of meta-xylene, ortho-xylene, para-xylene, and mixture thereof. In a particular example, the $C_6$-$C_{12}$ aromatic hydrocarbon is toluene. $C_1$-$C_6$ alcohol can be selected from: isopropanol, ethanol, methanol, n-butanol, tert-butanol, and n-propanol. For example, the alcohol is methanol.

The sulfuric acid and/or the mixture of the Varenicline base in solvents can be cooled prior to the addition of the sulfuric acid into the mixture. For example, it can be cooled to a temperature of about 0° to about 15° C., and, or to about 0° C. to about 5° C.

The sulfuric acid can be used as an about 10 percent to about 30 percent aqueous solution, or as an about 15 percent to about 25 percent aqueous solution, or as an about 20 percent vol/vol aqueous solution. The sulfuric acid can be used in excess.

The amount of the $C_6$-$C_{12}$ aromatic hydrocarbon and the alcohol solvent is in the range of about 5 percent to about 20 percent (vol/vol) $C_6$-$C_{12}$ aromatic hydrocarbon and about 80 percent to about 95 percent (vol/vol) $C_1$-$C_6$ alcohol, for example, methanol.

The reaction mixture can be cooled to a temperature of about 0° C. to about 15° C., about 0° C. to about 10° C., or about 0° C. to about 5° C.

The resulting precipitate may be recovered by various techniques, such as filtration. The precipitate may be dried under ambient or reduced pressure (pressure of less then about one atmosphere), and/or elevated temperature. The precipitate may be dried at room temperature at a pressure of about 400 to about 750 mm Hg and a temperature of about 40° C. to about 70° C.

In another embodiment, the invention provides Varenicline mesylate. The Varenicline mesylate can be isolated. The Varenicline mesylate can be also in a crystalline form.

In another embodiment, the invention provides a crystalline form of Varenicline mesylate, designated Form II.

Figure 2:
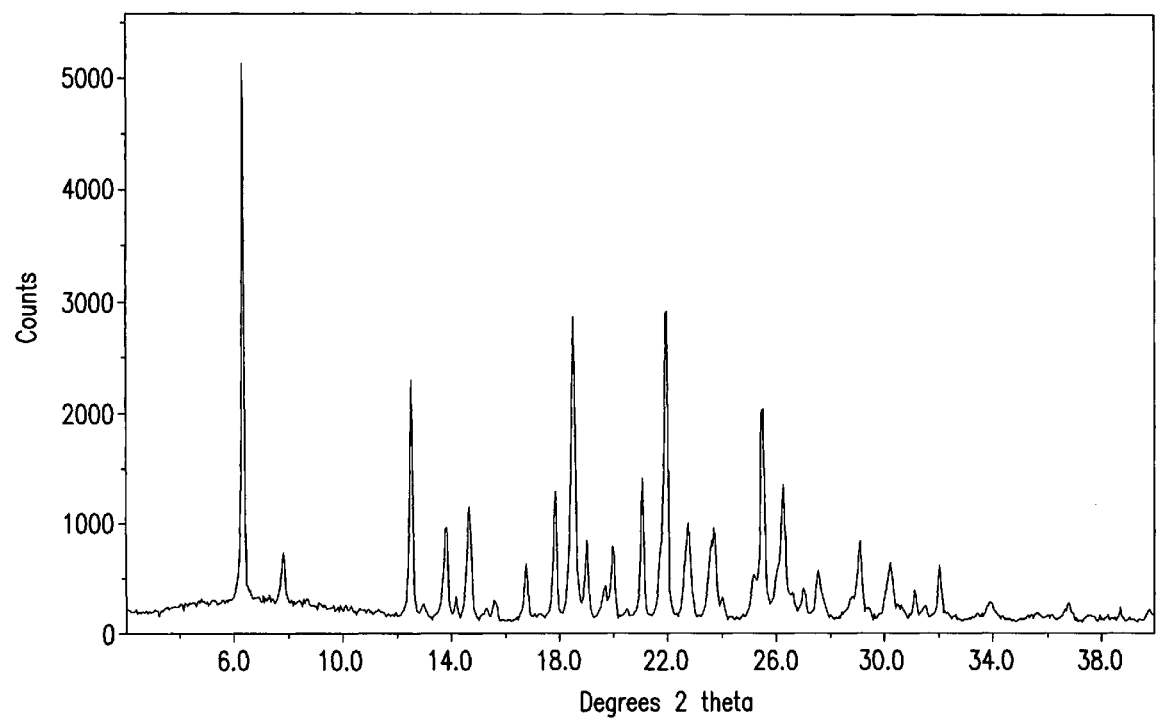
FIG. 2 shows a PXRD pattern of crystalline Form II of Varenicline Mesylate.

Form II can be characterized by analytical methods such as powder XRD and solid-state $^{13}C$ NMR. Form II is thus characterized by data selected from: a powder XRD pattern having peaks at 6.3°, 12.5°, 18.5°, 21.9°, and 25.5°±0.2 degrees two theta; a XRD pattern substantially as shown in FIG. 2; and combinations thereof. Form II may be further characterized by a additional powder XRD peaks at 13.7°, 14.6°, 17.8°, 21.0°, and 22.7°±0.2 degrees two theta.

Varenicline mesylate Form II preferably has advantageous properties selected from at least one of: high crystallinity, solubility, dissolution rate, morphology, low content of residual solvent, a lower degree of hygroscopicity, flowability, and advantageous processing and handling characteristics such as compressibility, and bulk density.

The invention also provides a crystalline form of Varenicline mesylate, designated Form III.

Figure 4:
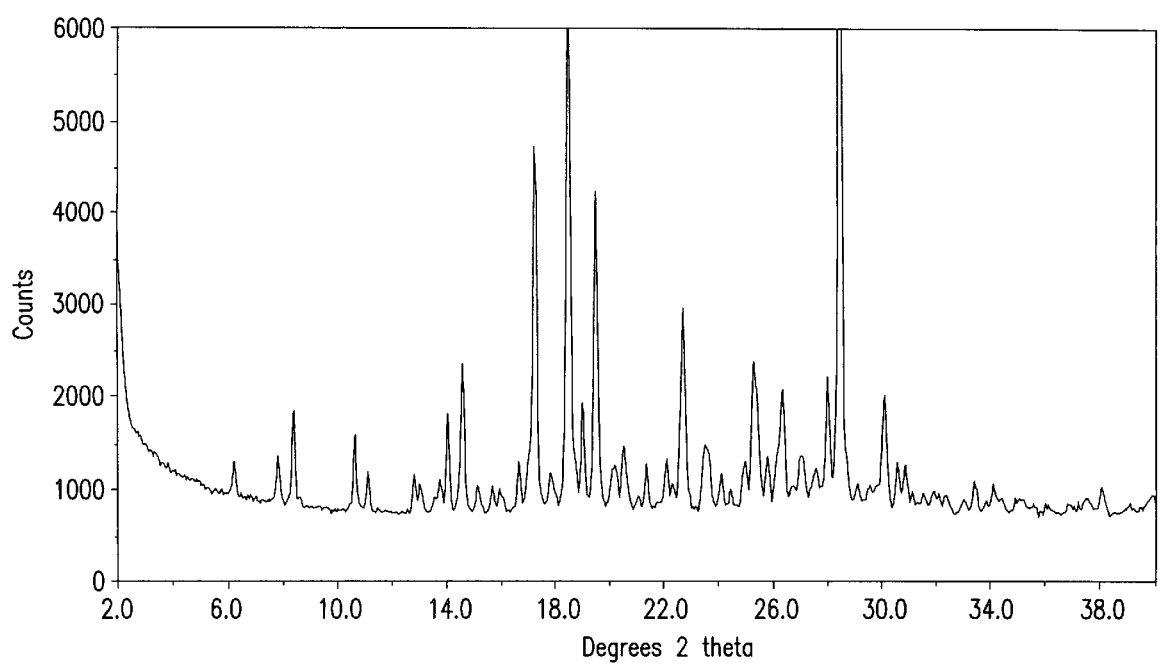
FIG. 4 shows a PXRD pattern of crystalline Form III of Varenicline mesylate.

Varenicline mesylate Form III can be characterized by data selected from: a powder XRD pattern having peaks at 8.4°, 10.7°, 11.1°, 17.3°, and 19.5°±0.2 degrees two theta; a XRD pattern as shown in FIG. 4; and combinations thereof. Form III may be further characterized by a additional powder XRD peaks at 12.8°, 14.0°, 14.6°, 18.5°, 25.2°±0.2 degrees two theta.

Figure 3:
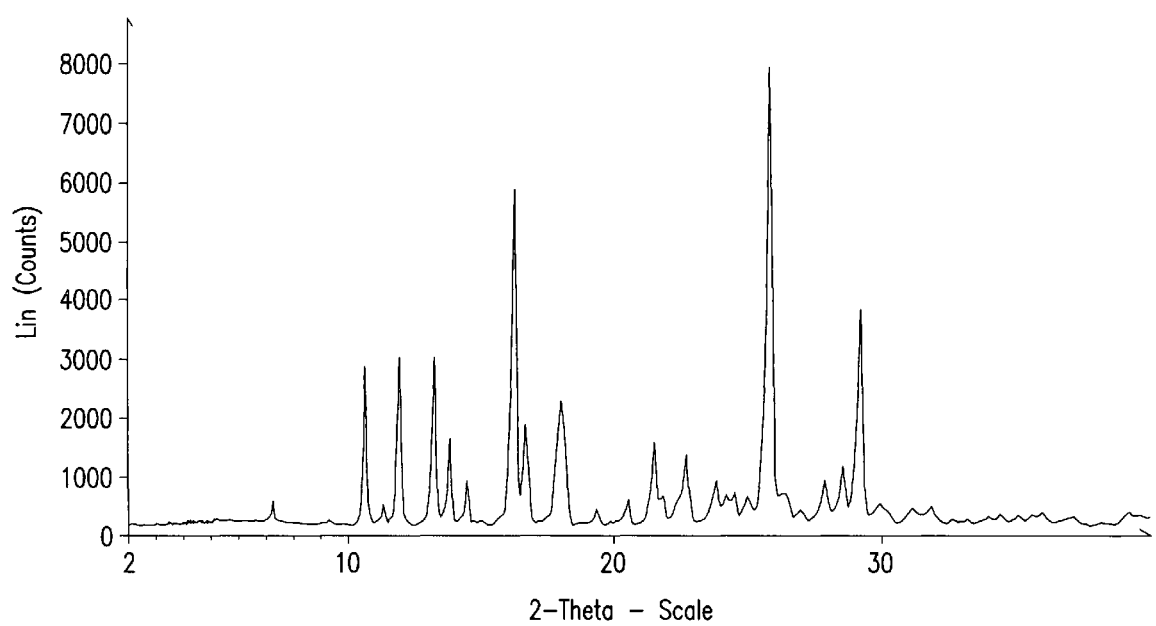
FIG. 3 shows a PXRD pattern of crystalline Form I of Varenicline Fumarate.

The invention also relates to a crystalline form of Varenicline fumarate, characterized by data selected from: a powder XRD pattern having peaks at 10.7°, 11.9°, 13.3°, 16.3°, and 18.0°±0.2 degrees two theta; a XRD pattern as shown in FIG. 3; and combination thereof. The above crystalline form of Varenicline Fumarate may be further characterized by additional powder XRD peaks at 13.8°, 16.6°, 21.5°, 22.7°, and 25.8°±0.2 degrees two theta.

The crystalline form of Varenicline fumarate may be prepared by a process comprising dissolving Varenicline base in a $C_1$-$C_6$ alcohol and contacting with fumaric acid to obtain a reaction mixture.

The heating in the process described above may be to a temperature of from about 50° C. to about 75° C., more preferably, from about 60° C. to about 75° C., and, most preferably, from about 65° C. to about 70° C.

The cooling in the process described above is to a temperature of from about 35° C. to about 10° C., more preferably, from about 32° C. to 15° C., and, most preferably, from about 30° C. to 20° C.

Preferably, the alcohol used in any of the processes described above is isopropyl alcohol (IPA), ethanol, n-butanol, tert-butanol, n-propanol, or methanol. Most preferably, the alcohol is methanol.

Preferably, the $C_6$-$C_{12}$ aromatic hydrocarbon used in any of the processes described above can be toluene or xylene, where the xylene can be used in the form of meta-xylene, ortho-xylene, para-xylene, and mixtures thereof. More preferably, the aromatic hydrocarbon is toluene.

Another aspect of the invention is a process for obtaining Varenicline base, comprising slurrying a Varenicline salt, for example, any of the Varenicline salts of the present invention, in water with a base and an inert organic solvent.

Not to be limited to any mechanism, the above reaction mixture leads to phase separation of organic and aqueous phases. Preferably, Varenicline base may be recovered from the organic phase.

Optionally, Varenicline base obtained in the process described above is further precipitated from the reaction mixture using an organic solvent. A suitable precipitating organic solvent is a $C_5$-$C_9$ alkane. Preferably the solvent is selected from a group consisting of pentane, hexane, and heptane. Most preferably, n-heptane is used.

The base used in the process described above is selected from alkali metal and alkaline earth metal carbonates, hydroxides, organic bases, and aqueous ammonia. More preferably, the base is selected from lithium carbonate, sodium carbonate, sodium bicarbonate, potassium carbonate, sodium hydroxide, and potassium hydroxide; $C_1$-$C_4$ alkyl amine, such as triethyl-amine, diisopropyl amine, and diisopropyl ethyl amine; di- and tri-hydroxy $C_1$-$C_4$ alkyl amine; morpholine, piperidine, pyridine and pyrrolidine, and aqueous ammonia. The base can be selected from lithium carbonate, sodium carbonate, sodium bicarbonate, potassium carbonate, sodium hydroxide, potassium hydroxide, and aqueous ammonia. For example, the base is sodium hydroxide.

The inert solvent used in the process described above is selected from $C_6$-$C_8$ aromatic hydrocarbons, $C_4$-$C_6$ esters, and $C_1$-$C_2$ halogenated hydrocarbons. For example, the solvent is selected from xylene, which can be in the form of meta-xylene, ortho-xylene, para-xylene, and mixtures thereof, benzene, toluene, butyl acetate, isopropyl acetate, ethyl acetate, ethylene dichloride, methylene dichloride, carbon tetrachloride, chloroform, and combinations thereof. For example, the inert solvent is toluene.

The reaction mixture in the process described above can be maintained at a temperature of about 30° C. to about 60° C., or about 40° C. to about 60° C.

The Varenicline salt used in the process described above can be combined with water and a base such as those described above. For example, a solution of Varenicline salt, such as Varenicline mesylate, Varenicline sulfate, or Varenicline fumarate in water is prepared. The base is then added to the solution to form a slurry. Varenicline can then be extracted out of the slurry into a water immiscible solvent. Suitable water immiscible solvents include $C_6$-$C_8$ aromatic hydrocarbons, $C_4$-$C_6$ esters and $C_1$-$C_2$ halogenated hydrocarbons. Examples for a suitable solvent are: xylene (can be used is a form of meta-xylene, ortho-xylene, para-xylene, and mixtures thereof), benzene, toluene, butyl acetate, isopropyl acetate, ethyl acetate, ethylene dichloride, methylene dichloride, carbon tetrachloride, chloroform, and combinations thereof.

The invention also provides a process for preparing Varenicline L-tartrate, comprising preparing a Varenicline salt according to any of the processes described above, and converting the Varenicline salt to Varenicline L-tartrate. Preferably, the conversion of the Varenicline salt to Varenicline L-tartrate comprises converting the Varenicline salt to Varenicline base according to any of the processes described above. Conversion of Varenicline base to Varenicline L-tartrate may be carried out according to methods known in the art, such as the one described in U.S. Pat. No. 6,890,927, incorporated herein by reference, wherein L-tartaric acid in methanol is combined with Varenicline base in methanol.

Varenicline base used in any of the processes described above may be obtained according to any known method in the art, such as the one described in U.S. Pat. No. 6,410,550, incorporated herein by reference, or directly from the following compound: 1-(5,8,14-triazatetracyclo[10.3.1.0$^{2,11}$.0$^{4,9}$] hexadeca-2(11),3,5,9-pentaene)-2,2,2-trifluoro-ethanone in the presence of methanol and a base, e.g., alkali metal, alkaline earth metal carbonates or hydroxides (as described in the examples of the present application), or by the methods in the examples herein.

The invention further encompasses 1) Varenicline sulfate, mesylate or fumarate, as described in any of the above embodiments for use as a medicament, 2) a pharmaceutical composition comprising any one, or combination, of solid state Forms, as described above and at least one pharmaceutically acceptable excipient and 3) the use of any one, or combination, of the above-described solid state Forms, in the manufacture of a pharmaceutical composition, 4) the use of any one or combination of the above described solid state Forms in a process for preparing Varenicline base or Varenicline tartrate. The pharmaceutical composition can be useful for the treatment of smoking addiction. The invention also provides crystalline forms as described above for use as a medicament, preferably for the treatment of smoking addiction.

Having described the invention with reference to certain preferred embodiments, other embodiments will become apparent to one skilled in the art from consideration of the specification. The disclosures of the references referred to in this patent application are incorporated herein by reference. The invention is further defined by reference to the following examples describing in detail the process and compositions of the invention. It will be apparent to those skilled in the art that many modifications, both to materials and methods, may be practiced without departing from the scope of the invention.

EXAMPLES

XRD

The X-ray powder diffraction patterns illustrated in FIGS. 1.2 and 3 were obtained using a Bruker X-Ray powder diffractometer Cu-tube, model D8 advance equipped with lynx-Eye position sensitive detector or equivalent. Measurements were taken at a wavelength of K$\alpha$=1.5406 Cu.

Sample holder: a standard sample holder of PMMA. (In case of low amount of material, standard sample holder of PMMA was used with zero background plate).

The X-Ray powder diffraction patterns illustrated in FIGS. 1.1 and 2 were obtained using an ARL X-ray powder diffractometer model X'TRA-019. A round zero background quartz plate was used. The cathode is CuKa radiation, $\lambda$=1.5418 Å. Scanning parameters: Range: 2-40 deg. 2 theta, continuous Scan, Rate: 3 deg/min, Step Size: 0.05. The accuracy of peak positions is defined as ±0.2 degrees due to experimental differences like instrumentations, and sample preparations.

$^{13}$C NMR Spectra:

$^{13}$C NMR spectra were obtained at 125 MHz using a Bruker Avance II+500 and SB probe using 4 mm rotors. Magic angle was set using KBr. Homogeneity of magnetic field checked using adamantane. Parameters for Cross polarization optimized using glycine. Spectral reference set according to glycine as external standard (176.03 ppm for low field carboxyl signal).

Magic Angle Spinning Rate:11 kHz

Pulse Program: cp with tppm15 during decoupling

Delay time: 5 s (except for Sitagliptin acetate, wherein the delay time was 10 s)

Contact time: 2 ms
Number of Scans: 1024
Scanning Parameters:
 Sample: Spin mode, rotation speed: 60 rpm.
Range: 2-40 degrees two-theta.
Scan mode: Continuous scan.
Step size: 0.05±0.005 deg.
Time/Step: 0.1 sec.
Divergon slit: 1
Procedure:
 Sample preparation: Gently grind a small amount of powder in an agate mortar with the pestle. Fill the powder in the round cavity of the sample holder by pressing with a glass plate or equivalent, to form a smooth surface that its height will not deviate from the sample holder's height.
HPLC Methodology
 Mobile Phase
Eluent A: 80%-0.02M Ammonium acetate; pH adjusted to 8.5 with diluted $NH_4OH$
 10%-MeOH
 10%-ACN
Eluent B: 20%-0.02M Ammonium acetate; pH adjusted to 8.5 with diluted $NH_4OH$
 50%-MeOH
 30%-CAN
 Diluent:
Eluent A
Chromatographic Conditions

| Column: | Purospher STAR RP-18e 75, 4 mm, 3 um. CN 1.51460.0001 or equivalent. |
| --- | --- |
| Flow | 1.0 ml/min |
| Injection Volume | 10 μl |
| Detector | 235 nm |
| Column temperature | 25° C. |
| Run time | 13 minutes |
| Equilibration time | 5 min |

Gradient Program

| Time (min) | % Eluent A | % Eluent B |
| --- | --- | --- |
| 0.0 | 100 | 0 |
| 7.0 | 60.0 | 40.0 |
| 13.0 | 0 | 100 |

Example 1

Preparation for 5,8,14-triazatetracyclo[10.3.1.0$^{2,11}$.0$^{4,9}$]hexadeca-2(11),3,5,7,9-pentaene Sulfate (Varenicline Sulfate)

In a clean and dry 4 neck round bottom flask equipped with mechanical stirrer and thermo pocket were charged methanol (19.8 ml), 1-(5,8,14-triazatetracyclo[10.3.1.0$^{2,11}$.0$^{4,9}$]hexadeca-2(11),3,5,9-pentaene)-2,2,2-trifluoro-ethanone (3.3 g, purity by HPLC: 98.90%) at 25° to 0° C. The mixture was treated with an aqueous solution of sodium hydroxide (0.86 g in 19.8 ml). The mixture was maintained at 20° to 30° C. for 1 hour. Then methanol was distilled out of the mixture under vacuum at 50° to 60° C. Toluene (16.5 ml) was then added to the reaction mixture, and the resulting mixture was stirred for 30 minutes. The resulting 2-phase mixture was separated, and the aqueous layer was extracted with toluene (4×16.5 ml). The toluene extract was concentrated, and then stripped out with methanol. The resulting residue was dissolved in methanol (4.7 ml), and treated with neutral alumina (0.2 g) and carbon (0.2 g) at reflux temperature for 1 hour. The mixture was then filtered through a celite bed at 45° to 55° C. (HPLC purity of crude Varenicline base in the reaction mass was 99.38 percent). To the above filtrate, pre-cooled 20 percent aqueous sulfuric acid solution (1.02 g in 5 ml demineralized water) was added at 0° to 5° C. A solid precipitated, and the mixture was stirred for 2 hours at 20° to 25° C., then filtered and washed with methanol (2 ml) to afford the product 5,8,14-triazatetracyclo[10.3.1.0$^{2,11}$.0$^{4,9}$]hexadeca-2(11),3,5,7,9-pentaene sulfate (Varenicline sulfate) (yield 22.98 percent, purity 99.81 percent)

Example 2

Preparation for 5,8,14-triazatetracyclo[10.3.1.0$^{2,11}$.0$^{4,9}$]hexadeca-2(11),3,5,7,9-pentaene (Varenicline Base)

In a clean and dry 4 neck round bottom flask equipped with mechanical stirrer and thermo pocket were charged demineralized water (2 ml), 5,8,14-triazatetracyclo[10.3.1.0$^{2,11}$.0$^{4,9}$]hexadeca-2(11),3,5,7,9-pentaene sulfate obtained in example 1 (Varenicline sulfate) (0.5 g) at 25° to 30° C. The mixture was treated with 30 percent aqueous solution of sodium hydroxide (1 ml) to adjust the pH to 12.5 to 13.5. The mixture was maintained at 20° to 30° C. for 0.5 hour. Toluene (5 ml) was then added, and the reaction mixture was heated to 50° to 60° C., and stirred for 30 minutes. The resulting 2-pase mixture was separated. The aqueous layer was adjusted to a pH of 12.5 to 13.5 using a 30 percent aqueous solution of sodium hydroxide, and was then extracted with toluene (4×5 ml). The combined toluene extract was treated with neutral alumina (0.01 g) and carbon (0.01 g) at 50° to 60° C. for 1 hour. The mixture was filtered through a celite bed at 50° to 60° C. The filtrate was then concentrated under vacuum at 50° to 60° C. The resulting residue was stirred in n-heptane (5 ml) for 1 hour. The thus-formed precipitate was filtered, and the filtered solid was washed with n-heptane (5 ml) to afford the product i.e. 5,8,14-Triazatetracyclo[10.3.1.0$^{2,11}$.0$^{4,9}$]hexadeca-2(11),3,5,7,9-pentaene (Varenicline Base). (Yield 83 percent, HPLC Purity 99.96 percent).

Example 3

Preparation for 5,8,14-triazatetracyclo[10.3.1.0$^{2,11}$.0$^{4,9}$]hexadeca-2(11),3,5,7,9-pentaene (Varenicline Base)

In a clean and dry 4 neck round bottom flask equipped with mechanical stirrer and thermo pocket were charged demineralized water (8 ml), 5,8,14-triazatetracyclo[10.3.1.0$^{2,11}$.0$^{4,9}$]hexadeca-2(11),3,5,7,9-pentaene mesylate obtained in example 8 (Varenicline mesylate) (2 g) at 25° to 30° C. The mixture was treated with a 30 percent aqueous solution of sodium hydroxide (2 ml) to adjust the pH to 12.5 to 13.5. The mixture was maintained to 20° to 30° for 0.5 hour. Toluene (10 ml) was then added, and the resulting mixture was heated to 50° to 60° C., and stirred for 30 minutes. The resulting 2-phase mixture was separated. The aqueous layer was adjusted to a pH of 12.5 to 13.5 using a 30 percent aqueous solution of sodium hydroxide, and was then extracted with toluene (4×10 ml). The combined toluene extract was treated with neutral alumina (0.2 g) and carbon (0.2 g) at 50° at 60° C. for 1 hour. This mixture was then filtered through a celite bed at 50° to 60° C. The filtrate was concentrated under vacuum at 50° to 60° C. The resulting residue was stirred in n-heptane (10 ml) for 1 hour. The resulting precipitate was filtered, and the filtered solid was washed with n-heptane (4 ml) to afford the product, 5,8,14-triazatetracyclo[10.3.1.0$^{2,11}$.0$^{4,9}$]hexadeca-2(11),3,5,7,9-pentaene (Varenicline Base). (Yield 70 percent, HPLC Purity 99.97 percent).

Example 4

Preparation for 5,8,14-triazatetracyclo[10.3.1.0$^{2,11}$.0$^{4,9}$]hexadeca-2(11),3,5,7,9-pentaene Fumarate (Varenicline Fumarate)

In a clean and dry 4 neck round bottom flask equipped with mechanical stirrer and thermo pocket were charged methanol (50 ml), 1-(5,8,14-triazatetracyclo[10.3.1.0$^{2,11}$.0$^{4,9}$]hexadeca-2(11),3,5,9-pentaene)-2,2,2-trifluoro-ethanone (8.3 g) at 25° to 30° C. The mixture was treated with an aqueous solution of sodium hydroxide (2.2 g in 50 ml). The resulting mixture was maintained to 20° to 30° C. for 1 hour. Then methanol was distilled out of the mixture under vacuum at 50° to 60° C. Toluene (42 ml) was added, and the resulting mixture was stirred for 30 minutes. The resulting 2-phase mixture was separated, and the aqueous layer was extracted with toluene (4×42 ml). The toluene extract was concentrated, and stripped out with methanol. The resulting residue was dissolved in methanol (12 ml), and treated with neutral alumina (0.5 g) and carbon (0.5 g) at reflux temperature for 1 hour. This mixture was then filtered through a celite bed at 45° to 55° C. (HPLC purity of crude Varenicline base in the reaction mass was 99.37 percent). To the above filtrate, fumaric acid (3.2 g) was added at 50° to 60° C. The resulting mixture was stirred for 2 hours at 65° to 70° C. to form a solution. The solution was then cooled to 20° to 30° C. A precipitate formed, and the mixture was stirred for 2 hours at 20° to 30° C. The mixture was then filtered, and the separated solid was washed with methanol (10 ml) to afford the product, 5,8,14-Triazatetracyclo[10.3.1.0$^{2,11}$.0$^{4,9}$]-hexadeca-2(11),3,5,7,9-pentaene fumarate (Varenicline Fumarate) (yield 73.88 percent, purity 99.98 percent)

Example 5

Preparation for 5,8,14-triazatetracyclo[10.3.1.0$^{2,11}$.0$^{4,9}$]hexadeca-2(11),3,5,7,9-pentaene (Varenicline Base)

In a clean and dry 4 neck round bottom flask equipped with mechanical stirrer and thermo pocket were charged demineralized water (12 ml), 5,8,14-Triazatetracyclo[10.3.1.0$^{2,11}$.0$^{4,9}$]hexadeca-2(11),3,5,7,9-pentaene fumarate obtained in example 4 (Varenicline fumarate) (3 g) at 25° to 30° C. This mixture was treated with a 30 percent aqueous solution of sodium hydroxide (6 ml) to adjust the pH to 12.5 to 13.5. The mixture was then maintained to 20° to 30° C. for 0.5 hour. Toluene (15 ml) was then added, and the resulting mixture was heated to 50° to 60° C., and stirred for 30 minutes. The resulting 2-phase mixture was separated. The aqueous layer was adjusted to a pH of 12.5 to 13.5 using a 30 percent aqueous solution of sodium hydroxide. The aqueous layer was then extracted with toluene (4×15 ml). The combined toluene extract was treated with neutral alumina (0.3 g) and carbon (0.3 g) at 50° to 60° C. for 1 hour. This mixture was then filtered through a celite bed at 50° to 60° C. The filtrate was concentrated under vacuum at 50° to 60° C. The resulting residue was stirred in n-heptane (10 ml) for 1 hour. The resulting precipitate was filtered, and the separated solid was washed with n-heptane (5 ml) to afford the product 5,8,14-triazatetracyclo[10.3.1.0$^{2,11}$.0$^{4,9}$]hexadeca-2(11),3,5,7,9-pentaene (Varenicline Base). (Yield 59.4 percent, HPLC Purity 99.96 percent).

Example 6

Preparation for 5,8,14-triazatetracyclo[10.3.1.0$^{2,11}$.0$^{4,9}$]hexadeca-2(11),3,5,7,9-pentaene Sulphate (Varenicline Sulphate)

In a clean and dry 4 neck round bottom flask equipped with mechanical stirrer and thermo pocket were charged methanol (192 ml),1-(5,8,14-triazatetracyclo[10.3.1.0$^{2,11}$.0$^{4,9}$]hexadeca-2(11),3,5,9-pentaene)-2,2,2-trifluoro-ethanone (32.0 g, purity by HPLC: 99.38%) at 20-30° C. The mixture was treated with an aqueous solution of sodium hydroxide (8.338 g in 192 ml). The resulting mixture was maintained at 20-30° C. for one hour. Then, methanol was distilled out of the mixture under vacuum at 50-60° C. Toluene (160 ml) was added to the reaction mixture, and the resulting mixture was stirred for 30 minutes. The resulting 2-phase mixture was separated. The aqueous layer was extracted with toluene (4×160 ml). The toluene extract was concentrated, and stripped out with methanol. The resulting residue was dissolved in methanol (45.6 ml), and further treated with neutral alumina (2.0 g) and carbon (2.0 g) at reflux temperature for 1 hour. The mixture was then filtered through a celite bed at 45-55° C. (HPLC purity of crude Varenicline base: 98.90). To the above filtrate was added pre-cooled 20% aqueous sulphuric acid solution (9.89 g in 48.48 ml DM water) at 0-5° C. A precipitate formed, and this mixture was stirred for 2 hrs at 20-25° C. The mixture was then filtered, and the separated solid was washed with methanol (20 ml) to afford the product 5,8,14-Triazatetracyclo[10.3.1.0$^{2,11}$.0$^{4,9}$]hexadeca-2(11),3,5,7,9-pentaene sulphate (Varenicline sulphate) (yield 28.7%, purity 99.88%).

Example 7

Preparation for 5,8,14-triazatetracyclo[10.3.1.0$^{2,11}$.0$^{4,9}$]hexadeca-2(11),3,5,7,9-pentaene Fumarate (Varenicline Fumarate)

In a clean and dry 4 neck round bottom flask equipped with mechanical stirrer and thermo pocket were charged methanol (60 ml), 1-(5,8,14-triazatetracyclo[10.3.1.0$^{2,11}$.0$^{4,9}$]hexadeca-2(11),3,5,9-pentaene)-2,2,2-trifluoro-ethanone (10.0 g) at 20-30° C. This mixture was treated with an aqueous solution of sodium hydroxide (2.605 g in 60 ml). The resulting mixture was maintained to 20-30° C. for 1 hour. Then, methanol was distilled out of the mixture under vacuum at 50-60° C. Toluene (50 ml) was added to the reaction mixture, and the resulting mixture was stirred for 30 minutes. The resulting 2-phase mixture was separated. The aqueous layer was extracted with toluene (4×50 ml). The toluene extract was concentrated, and stripped out with methanol. The resulting residue was dissolved in methanol (14.45 ml), and further treated with neutral alumina (0.6 g) and activated carbon (0.6 g) at reflux temperature for one hour. This mixture was filtered through a celite bed at 45-55° C. To the filtrate was added fumaric acid (3.855 g) at 50-60° C. This mixture was stirred for 2 hrs at 65-70° C. The mixture was then cooled to 20-30° C. A precipitate formed, and this mixture was stirred for 2 Hr at 20-30° C., then filtered, and the separated solid was washed with methanol (12 ml) to afford the product 5,8,14- triazatetracyclo[10.3.1.0$^{2,11}$.0$^{4,9}$]hexadeca-2(11),3,5,7,9-pentaene fumarate (Varenicline Fumarate). Yield 72.0%, purity 99.56%.

Example 8

Preparation for Form II of 5,8,14-triazatetracyclo [10.3.1.0$^{2,11}$.0$^{4,9}$]hexadeca-2(11),3,5,7,9-pentaene Mesylate (Varenicline Mesylate)

In a clean and dry 4 neck round bottom flask equipped with mechanical stirrer and thermo pocket were charged 5,8,14-triazatetracyclo[10.3.1.0$^{2,11}$.0$^{4,9}$]hexadeca-2(11),3,5,9-pentaene (Varenicline base)(2 g purity-98.37%) in acetone (74 ml) at 20-30° C. The resulting mixture was stirred at 20-30° C. to provide a clear solution. To this solution was added methane sulphonic acid solution in acetone (1.2 g in 14 ml acetone) over 5-10 minutes at 20-30° C. A precipitate formed, and this mixture was stirred for 1 hour at 20-30° C. The mixture was then filtered under nitrogen, and the separated solid was washed with acetone (10 ml) to afford 5,8,14-triazatetracyclo[10.3.1.0$^{2,11}$.0$^{4,9}$]hexadeca-2(11),3,5,7,9-pentaene mesylate (Varenicline mesylate).yield—1.25 w/w, purity—99.60%).

Example 9

Preparation for Form II of 5,8,14-triazatetracyclo [10.3.1.0$^{2,11}$.0$^{4,9}$]hexadeca-2(11),3,5,7,9-pentaene Mesylate (Varenicline Mesylate)

In a clean and dry 4 neck round bottom flask equipped with mechanical stirrer and thermo pocket were charged 5,8,14-Triazatetracyclo[10.3.1.0$^{2,11}$.0$^{4,9}$]hexadeca-2(11),3,5,9-pentaene (Varenicline base)(10 g purity-99.72%) in acetone (370 ml) at 20-30° C. The resulting mixture was stirred at 20-30° C. to form a clear solution. To this solution was added methane sulphonic acid solution in acetone (6.0 g in 70 ml acetone) in 10-20 minutes at 20-30° C. A precipitate formed, and this mixture was stirred for 1 hour at 20-30° C. The mixture was then filtered under nitrogen, and the separated solid was washed with acetone (50 ml) to afford 5,8,14-triazatetracyclo[10.3.1.0$^{2,11}$.0$^{4,9}$]hexadeca-2(11),3,5,7,9-pentaene mesylate (Varenicline mesylate).yield—1.38 w/w, purity—99.78%).

Example 10

Preparation for Form II of 5,8,14-triazatetracyclo [10.3.1.0$^{2,11}$.0$^{4,9}$]hexadeca-2(11),3,5,7,9-pentaene Mesylate (Varenicline Mesylate)

In a clean and dry 4 neck round bottom flask equipped with mechanical stirrer and thermo pocket were charged 5,8,14-triazatetracyclo[10.3.1.0$^{2,11}$.0$^{4,9}$]hexadeca-2(11),3,5,9-pentaene (Varenicline base)(15 g purity-99.72%) in acetone (555 ml) at 20-30° C. The resulting mixture was stirred at 20-30° C. to provide a clear solution. To this solution was added methane sulphonic acid solution in acetone (9.0 g in 105 ml acetone) over 10-20 minutes at 20-30° C. A precipitate formed, and this mixture was stirred for 1 hour at 20-30° C. The mixture was then filtered under nitrogen, and the separated solid was washed with acetone (75 ml) to afford 5,8,14-triazatetracyclo[10.3.1.0$^{2,11}$.0$^{4,9}$]hexadeca-2(11),3,5,7,9-pentaene mesylate (Varenicline mesylate). Yield—1.43 w/w, purity—99.79%)

Example 11

Preparation for Form II of 5,8,14-triazatetracyclo [10.3.1.0$^{2,11}$.0$^{4,9}$]hexadeca-2(11),3,5,7,9-pentaene Mesylate (Varenicline Mesylate)

In a clean and dry 4 neck round bottom flask equipped with mechanical stirrer and thermo pocket were charged 5,8,14-triazatetracyclo[10.3.1.0$^{2,11}$.0$^{4,9}$]hexadeca-2(11),3,5,9-pentaene (Varenicline base)(15 g purity-99.72%) in acetone (555 ml) at 20-30° C. The resulting mixture was stirred at 20-30° C. to provide a clear solution. To this solution was added methane sulphonic acid solution in acetone (9.0 g in 105 ml acetone) over 10-20 minutes at 20-30° C. A precipitates formed, and this mixture was stirred for 1 hour at 20-30° C. The mixture was then filtered under nitrogen, and the separated solid was washed with acetone (75 ml) to afford 5,8,14-triazatetracyclo[10.3.1.0$^{2,11}$.0$^{4,9}$]hexadeca-2(11),3,5,7,9-pentaene mesylate (Varenicline mesylate). Yield—1.4 w/w, purity—99.74%.

Example 12

Preparation for Form II of 5,8,14-triazatetracyclo [10.3.1.0$^{2,11}$.0$^{4,9}$]hexadeca-2(11),3,5,7,9-pentaene Mesylate (Varenicline Mesylate)

In a clean and dry 4 neck round bottom flask equipped with mechanical stirrer and thermo pocket were charged 5,8,14-triazatetracyclo[10.3.1.0$^{2,11}$.0$^{4,9}$]hexadeca-2(11),3,5,9-pentaene (Varenicline base)(15 g purity—99.72%) in acetone (555 ml) at 20-30° C. The resulting mixture was stirred at 20-30° C. to provide a clear solution. To this solution was added a methane sulphonic acid solution in acetone (9.0 g in 105 ml acetone) over 10-20 minutes at 20-30° C. A precipitate formed, and this mixture was stirred for 1 hour at 20-30° C. This mixture was then filtered under nitrogen, and the separated solid was washed with acetone (75 ml), and further dried at 30-35° C. in a vacuum oven for 12 hrs to afford the product, 5,8,14-triazatetracyclo[10.3.1.0$^{2,11}$.0$^{4,9}$]hexadeca-2(11),3,5,7,9-pentaene mesylate (Varenicline mesylate). Yield—1.43 w/w, purity—99.79%.

Example 13

Preparation for Form III of 5,8,14-triazatetracyclo [10.3.1.0$^{2,11}$.0$^{4,9}$]hexadeca-2(11),3,5,7,9-pentaene Mesylate (Varenicline Mesylate)

Varenicline mesyalte form II was kept under 40° C. for 5 days. Varenicline mesyalte form III was obtained and analyzed by XRD.

What is claimed:

1. Varenicline sulfate Form I, characterized by a powder X-ray diffraction pattern having peaks at 15.1°, 15.4°, 16.8°, 17.7°, and 21.5°±0.2 degrees two theta.

2. The varenicline sulfate Form I of claim 1, further characterized by additional powder X-ray diffraction peaks at 10.3°, 19.0°, 19.9°, and 22.2°±0.2 degrees two theta.

3. The varenicline sulfate Form I of claim 1, further characterized by a solid-state $^{13}$C NMR spectrum having chemical shift differences between the signal exhibiting the lowest chemical shift and another in the chemical shift range of 120 to 180 ppm of 0.0, 13.7, and 21.0±0.1 ppm, wherein the signal exhibiting the lowest chemical shift in the chemical shift area of 120 to 180 ppm is at 124.0±1 ppm.

4. The varenicline sulfate Form I of claim 1, characterized by a powder X-ray diffraction pattern as shown in FIG. 1.1.

5. The varenicline sulfate Form I of claim 1, characterized by a $^{13}$C NMR spectrum as shown in FIG. 1.2.

6. A pharmaceutical composition comprising the varenicline sulfate Form I of claim 1, and at least one pharmaceutically acceptable excipient.

* * * * *